United States Patent [19]
Mederski et al.

[11] Patent Number: 6,037,349
[45] Date of Patent: *Mar. 14, 2000

[54] IMIDAZOPYRIDINES

[75] Inventors: Werner Mederski, Erzhausen; Johannes Sombroek, Darmstadt; Pierre Schelling, Mühltal; Norbert Beier, Reinheim; Ingeborg Lues, Darmstadt; Klaus-Otto Minck, Ober-Ramstadt, all of Germany

[73] Assignee: Merck Patent GmbH, Germany

[*] Notice: This patent is subject to a terminal disclaimer.

[21] Appl. No.: 09/224,355

[22] Filed: Jan. 4, 1999

Related U.S. Application Data

[63] Continuation of application No. 08/725,242, Oct. 4, 1996, Pat. No. 5,798,364, and a continuation of application No. 08/182,321, Jan. 18, 1994, abandoned, and a continuation-in-part of application No. 08/034,954, Mar. 22, 1993, abandoned, and a division of application No. 07/857,855, Mar. 26, 1992, abandoned.

[30] Foreign Application Priority Data

Mar. 27, 1991 [DE] Germany ............... 41 10 019

[51] Int. Cl.$^7$ ............ C07D 471/02; A61K 31/415; A61K 31/44
[52] U.S. Cl. ............ 514/303; 514/81; 514/263; 514/265; 546/118
[58] Field of Search ............ 514/81, 263, 265, 514/303; 546/118

[56] References Cited

U.S. PATENT DOCUMENTS

| | | | |
|---|---|---|---|
| 3,235,357 | 2/1966 | Loux | 504/243 |
| 4,880,804 | 11/1989 | Carini et al. | 514/234.5 |
| 5,073,566 | 12/1991 | Lifer et al. | |
| 5,102,880 | 4/1992 | Chakravarty | 514/212 |
| 5,157,026 | 10/1992 | Chakravarty et al. | 514/81 |
| 5,223,499 | 6/1993 | Greenlee et al. | 514/234.5 |
| 5,240,938 | 8/1993 | Greenlee et al. | 514/303 |
| 5,242,928 | 9/1993 | Mederski et al. | 514/303 |
| 5,476,857 | 12/1995 | Mederski | 514/303 |
| 5,532,276 | 7/1996 | Mederski | 514/303 |
| 5,798,364 | 8/1998 | Mederski | 514/81 |

FOREIGN PATENT DOCUMENTS

| | | |
|---|---|---|
| 392317 | 4/1990 | European Pat. Off. |
| 399731 | 11/1990 | European Pat. Off. |
| 400974 | 12/1990 | European Pat. Off. |
| 468470 | 7/1991 | European Pat. Off. |
| 91/14367 | 10/1991 | WIPO |

OTHER PUBLICATIONS

W. Grassmann et al., Chem. Ber. vol. 99, No. 1 (1966) pp. 244–253.
Chemical Abstracts, vol. 109, 1988, Frf. 73432w.
Chemical Abstracts vol. 110, 1989, Ref. 160371q.
Chemical Abstracts, vol. 112, 1990, Ref. 139030j.
Chemical Abstracts, vol. 112, 1990, Ref. 216932j.
Chiu et al., J. of Pharm. and Exper. Ther., vol. 250, No. 3, pp. 867–874 (May 22, 1989).
Wong et al., J. of Pharm. and Exper. Ther., vol. 252, No. 2., pp. 719–725 (Oct. 26, 1989).
Chem. Abstracts 121:83197, 1994.
Chem. Abstracts 119:203420, 1993.
Chem. Abstracts 118:254907, 1992.

*Primary Examiner*—D. Margaret Seaman
*Attorney, Agent, or Firm*—Millen, White, Zelano & Branigan, P.C.

[57] ABSTRACT

Imidazopyridine derivatives ad pharmacologically acceptable salts having antagonistic properties towards angiotensin II can be used for the treatment of hypertension, aldosteronism and cardiac insufficiency.

13 Claims, No Drawings

IMIDAZOPYRIDINES

This application is a continuation of application Serial No. 08/725,242 filed Oct. 4, 1996, now U.S. Pat. No. 5,798,364, which is a continuation of application Ser. No. 08/182,321, filed Jan. 18, 1994, now abandoned, which is a continuation-in-part of application Serial No. 08/034,954 filed Mar. 22, 1993, now abandoned, which is a divisional application of application Ser. No. 07/857,855 filed Mar. 26, 1992, now abandoned, all of which are herein incorporated by reference.

SUMMARY OF THE INVENTION

The invention relates to novel imidazopyridine derivatives of formula I:

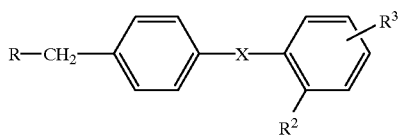

in which R is (a)

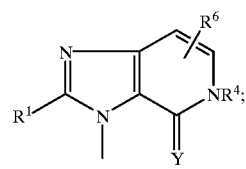

(b)

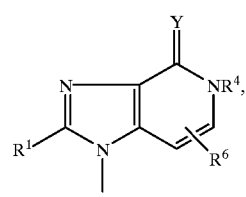

(c)

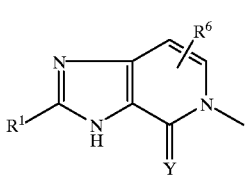

or (d)

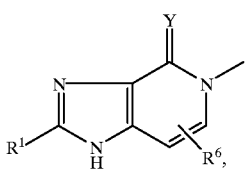

$R^1$ is A, alkenyl or alkynyl having up to 6 C atoms in each case,
$R^2$ is COOH, COOA, CN, $NO_2$, $NH_2$, $NHCOR^5$, $NHSO_2R^5$ or tetrazol-5-yl,
$R^3$ is H, Hal, A, OA or $NO_2$,
$R^4$ is H, $R^5$, cyanoalkyl, AOOC-alkyl, carboxyalkyl or tetrazol-5-ylalkyl having 1–6 C atoms in the "alkyl" moiety in each case, alkenyl or alkynyl having up to 6 C atoms in each case, aralkyl having 7–11 C atoms which is unsubstituted or mono- or disubstituted by Hal, $R^5$, COOH, COOA, CN, $NO_2$, $NH_2$, NHA, $N(A)_2$, $NHCOR^5$, NHCOOA, $NHSO_2R^5$, OH, OA or tetrazol-5-yl, or

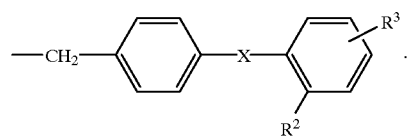

$R^5$ is alkyl having 1–4 C atoms, in which one or more H atoms can also be replaced with F,
$R^6$ is H or Hal,
X is absent or is —CO—, —O—, —NH—CO—, —CO—NH—, $CH_2O$— or —O—$CH_2$—,
Y is O or S,
A is alkyl having 1–6 C atoms and
Hal is F, Cl, Br or I, and their salts.

Similar compounds are known from European patent document A2-0 400 974.

The object of the invention was to find novel compounds with valuable properties, especially those which can be used for the preparation of drugs.

It was found that the compounds of formula I and their salts possess very valuable pharmacological properties coupled with a good tolerance. In particular, they have antagonistic properties towards angiotensin II and can therefore be used for the treatment of angiotensin II-dependent hypertension, aldosteronism and cardiac insufficiency. These effects can be determined by conventional in vitro or in vivo methods such as e.g. those described in U.S. Pat. No. 4,880,804 and also by A. T. Chiu et al., J. Pharmacol. Exp. Therap. 250, 867–874 (1989), and by P. C. Wong et al., ibid. 252, 719–725 (1990; in vivo, on rats).

The compounds of formula I can be used as pharmaceutical active ingredients in human and veterinary medicine, especially for the prophylaxis and/or therapy of cardiac, circulatory and vascular diseases, in particular of hypertonia, cardiac insufficiency and hyperaldosteronism.

The invention relates to the compounds of formula I and their salts and to a process for the preparation of these compounds and their salts, characterized in that (a) a compound of formula II:

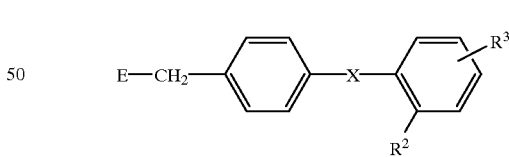

in which E is Cl, Br, I, a free OH group or an OH group which has been functionally modified to acquire reactivity, and $R^2$, $R^3$ and X are as defined in claim 1, is treated with a compound of formula III:

H—R  III in which R is as defined in claim 1, or (b) to prepare a compound of formula I in which $R^4$ is H and Y is O, a compound of formula IV:

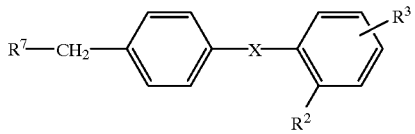

in which $R^7$ is

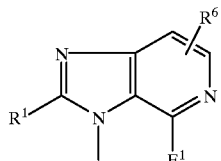

or

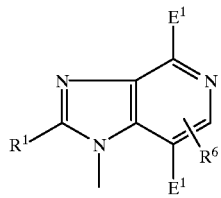

$E^1$ is Cl, Br, I or an OH group which has been functionally modified to acquire reactivity, and $R^1$, $R^2$, $R^3$, $R^6$ and X are as defined in claim 1, is treated with a solvolyzing agent, or c) a compound of formula V:

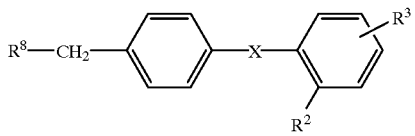

in which $R^8$ is

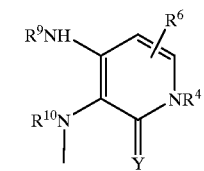

or

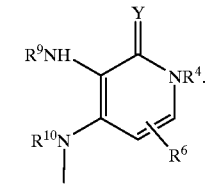

$R^9$ is $R^1$—CO or H, $R^{10}$ is H (if $R^9$ is $R^1$—CO) or $R^1$—CO (if $R^9$ is H) and $R^1$, $R^2$, $R^3$, $R^4$, $R^6$, X and Y are as defined in claim 1, is treated with a cyclizing agent, or (d) to prepare a compound of formula I in which X is —NH—CO— or —CO—NH—, a compound of formula VI:

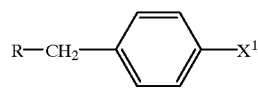

in which $X^1$ is $NH_2$ or COOH and R is as defined in claim 1, or a reactive derivative of this compound is reacted with a compound of formula VII:

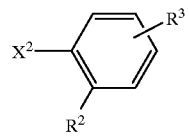

in which $X^2$ is COOH (if $X^1$ is $NH_2$) or $NH_2$ (if $X^1$ is COOH) and $R^2$ and $R^3$ are as defined in claim 1, or with a reactive derivative of this compound, or (e) to prepare a compound of formula I in which X is $CH_2$—O— or —O-$CH_2$—, a compound of formula VIII:

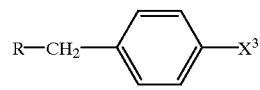

in which $X^3$ is $CH_2E$ or OH and R is as defined in claim 1, or a reactive derivative of this compound is reacted with a compound of formula IX:

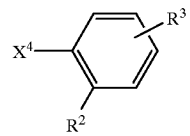

in which $X^4$ is OH (if $X^3$ is $CH_2E$) or $CH_2E$ (if $X^3$ is OH) and $R^2$ and $R^3$ are as defined in claim 1, or with a reactive derivative of this compound, or (f) to liberate a compound of formula I by treatment of one of its functional derivatives with a solvolyzing or hydrogenolyzing agent, and/or in that one or more radicals R, $R^2$ and/or $R^3$ in a compound of formula I are converted to one or more other radicals R, $R^2$ and/or $R^3$, and/or a base or acid of formula I is converted to one of its salts.

Above and below, unless expressly stated otherwise, the radicals or parameters R, $R^1$ to $R^{10}$, X, Y, A, Hal, E, $E^1$, $X^1$, $X^2$, $X^3$ and $X^4$ are as defined in formulae I to IX.

In the above formulae, A has 1–6, preferably 1, 2, 3 or 4 C atoms. A is preferably methyl, or else ethyl, propyl, isopropyl, butyl, isobutyl, sec-butyl or tert-butyl, or else pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl or 1,1,2- or 1,2,2-trimethylpropyl. Alkenyl is preferably vinyl, prop-1-enyl or prop-2-enyl or but-1-enyl, or else pent-1-enyl or hex-1-enyl. Alkynyl is preferably ethynyl or prop-1-ynyl or prop-2-ynyl, or else but-1-ynyl, pent-1-ynyl or hex-1-ynyl.

Hal is preferably F, Cl or Br, or else I.

R is a radical derived from 3H-imidazo[4,5-c]-pyridine [(cases (a) and (c)] or a radical derived from 1H-imidazo [4,5-c]pyridine [cases (b) and (d)] or, more precisely:

2-$R^1$-4-(thi)oxo-5-$R^4$-6(or 7)-$R^6$-4,5-dihydro-3H-imidazo[4,5-c]pyridin-3-yl, (b) 2-$R^1$-4-(thi)oxo-5-$R^4$-6(or 7)-$R^6$-4,5-dihydro-1H-imidazo[4,5-c]pyridin-1-yl, (c) 2-$R^1$-4-(thi)oxo-6(or 7)-$R^6$-4,5-dihydro-3H-imidazo[4,5-c]pyridin-5-yl, (d) 2-$R^1$-4-(thi)oxo-6(or 7)-$R^6$-4,5-dihydro-1H-imidazo[4,5-c]pyridin-5-yl.

Accordingly, the compounds of formula I include those of formula Ia, in which R is as defined under (a), those of formula Ib, in which R is as defined under (b), those of formula Ic, in which R is as defined under (c), and those of formula Id, in which R is as defined under (d). The compounds of formula Ia are preferred. The compounds of formulae Ic and Id are tautomeric and normally exist as a mixture.

Preferably, the radical $R^1$ is linear and is A, alkenyl or alkynyl having 3–6 C atoms in each case, especially butyl, or else propyl, pentyl, hexyl, allyl or prop-1-enyl, or else but-1-enyl, pent-1-enyl, hex-1-enyl, prop-1-ynyl, but-1-ynyl, pent-1-ynyl or hex-1-ynyl.

The radical $R^2$ is preferably CN, or else preferably tetrazol-5-yl, COOH, COOCH$_3$, COOC$_2$H$_5$ or NHSO$_2$CF$_3$.

The radical $R^3$ is preferably H.

The radical $R^4$ is preferably H, or else preferably $R^5$ (especially CH$_3$, CF$_3$, C$_2$F$_5$, CH$_2$CF$_3$, CH$_2$CH$_2$CF$_3$), cyanoalkyl (especially cyanomethyl, 2-cyanoethyl, 3-cyanopropyl), AOOC-alkyl (especially methoxycarbonylmethyl, ethoxycarbonylmethyl, 2-methoxycarbonylethyl, 2-ethoxycarbonylethyl), carboxyalkyl (especially carboxymethyl, 2-carboxyethyl, 3-carboxypropyl) or tetrazol-5-ylalkyl [especially tetrazol-5-ylmethyl, 2-(tetrazol-5-yl)ethyl, 3-(tetrazol-5-yl)propyl], it being possible for all these radicals to contain a total of up to 6 C atoms in each case. Also, the radical $R^4$ is preferably unsubstituted or monosubstituted (preferably in o-position) or disubstituted (preferably in 2,6-position) aralkyl having 7–11 C atoms, especially benzyl, 1- or 2-phenylethyl, 1-, 2- or 3-phenylpropyl, 1-, 2-, 3- or 4-phenylbutyl, o-, m- or p-fluorobenzyl, (preferably) o-, m- or p-chlorobenzyl, o-, m- or p-bromobenzyl, o-, m- or p-methyl-benzyl, o-, m- or p-trifluoromethylbenzyl, o-, m- or p-methoxycarbonylbenzyl, o-, m- or p-ethoxycarbonylbenzyl, (preferably) o-, m- or p-cyanobenzyl, o-, m- or p-carboxybenzyl, o-, m- or p-nitrobenzyl, o-, m- or p-aminobenzyl, o-, m-, or p-methylaminobenzyl, o-, m-, or p-ethylaminobenzyl, o-, m- or p-isopropylaminobenzyl, o-, m- or p-dimethylaminobenzyl, o-, m- or p-acetamidobenzyl, o-, m- or p-pentanamidobenzyl, o-, m- or p-trifluoracetamidobenzyl, o-, m- or p-methoxycarbonylaminobenzyl, o-, m- or p-tert.-butoxycarbonylaminobenzyl, o-, m- or p-trifluormethylsulfonamidobenzyl, o-, m- or p-hydroxybenzyl, o- , m- or p-methoxybenzyl, (preferably) o-, m- or p-(tetrazol-5-yl)benzyl, 2,3,-, 2,4-, 2,5-, (preferably) 2,6-, 3,4- or 3,5-difluorbenzyl, 2,3-, 2,4-, 2,5-, (preferably) 2,6-, 3,4- or 3,5-dichlorobenzyl, 2-chloro-6-fluoro-benzyl, 2-chloro-6-methyl-benzyl, 2-fluoro-6-trifluoromethyl-benzyl, 2-chloro-6-trifluoromethyl-benzyl, 2-fluoro-6-carboxy-benzyl , 2-fluoro-6-methoxycarbonyl-benzyl, 2-fluoro-6-nitro-benzyl, 2-fluoro-6-amino-benzyl, 2-chloro-6-nitro-benzyl, 2-chloro-6-amino-benzyl, 2,3-, 2,4-, 2,5-, (preferably) 2,6-,3,4- or 3,5-dimethoxybenzyl. Also, the radical $R^4$ can preferably be

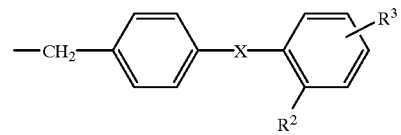

Preferably, the radical $R^5$ contains 1, 2 or 3 C atoms and is methyl, ethyl, trifluoromethyl, pentafluoro-ethyl, 2,2,2-trifluoroethyl or 3,3,3-trifluoropropyl.

The radical $R^6$ is preferably H or Cl.

Preferably, the radical X is absent or is —NHCO—or —CO—NH—.

The radical Y is preferably O.

The compounds of formula I can possess one or more chiral centers and can therefore exist in different forms (optically active or optically inactive). Formula I includes all these forms.

Accordingly, the invention relates especially to those compounds of formula I in which at least one of said radicals has one of the preferred meanings indicated above. Some preferred groups of compounds can be expressed by the following partial formulae Ie to Ik, Iae to Iak, Ibe to Ibk, Ice to Ick and Ide to Idk, which correspond to formulae I and Ia to Id and in which the radicals not described more precisely are as defined in formulae I and Ia to Id:

compounds of formulae Ie and Iae, Ibe, Ice and Ide, which correspond to formulae I and Ia to Id except that in addition X is absent;

compounds of formulae If and Iaf, Ibf, Icf and Idf, which correspond to formulae I and Ia to Id except that in addition X is —CO—;

compounds of formulae Ig and Iag, Ibg, Icg and Idg, which correspond to formulae I and Ia to Id except that in addition X is —O—;

compounds of formulae Ih and Iah, Ibh, Ich and Idh, which correspond to formulae I and Ia to Id except that in addition X is —NH—CO—;

compounds of formulae Ii and Iai, Ibi, Ici and Idi, which correspond to formulae I and Ia to Id except that in addition X is —CO—NH—;

compounds of formulae Ij and Iaj, Ibj, Icj and Idj, which correspond to formulae I and Ia to Id except that in addition X is —CH$_2$—O—; and compounds of formulae Ik and Iak, Ibk, Ick and Idk, which correspond to formulae I and Ia to Id except that in addition X is —O—CH$_2$—.

Of the above compounds, those of formula Ie and especially those of formulae Iae and Ibe are particularly preferred.

Very particularly preferred compounds are those of formulae I and Ia to Ik, Iae to Ide, Iaf to Idf, Iag to Idg, Iah to Idh, Iai to Idi, Iaj to Idj and Iak to Idk in which in addition $R^3$, $R^4$ and/or $R^6$ are H and/or Y is O.

Among these, preferred compounds are those in which $R^2$ is CN, COOH, COOCH$_3$, COOC$_2$H$_5$, NHSO$_2$CF$_3$ or tetrazol-5-yl.

A very particularly preferred group of compounds has formula I in which

R is 2-A-4,5-dihydro-4-oxo-5-$R^4$-1H-imidazo[4,5-c]pyridin-1-yl, 2-A-4,5-dihydro-4-oxo-5-$R^4$-3H-imidazo[4,5-c]pyridin-3-yl, 2-A-4,5-dihydro-4-oxo-5-$R^4$-1H-imidazo[4,5-c]pyridin-5-yl or 2-A-4,5-dihydro-4-oxo-5-$R^4$-3H-imidazo[4,5-c]pyridin-5-yl, $R^2$ is COOH, COOCH$_3$, CN or tetrazol-5-yl,
$R^3$ is H, $R^4$ is H or

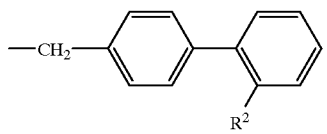

and X is absent.

A small selected group of preferred compounds has formula I in which
R is a 2-butyl-4,5-dihydro-4-oxo-3H-imidazo[4,5-c]-pyridin-3-yl radical,
$R^2$ is COOH, COOCH$_3$, CN or tetrazol-5-yl,
$R^3$ is H,
Y is O and
X is absent.

Another selected group of preferred compounds has formula I in which $R^2$ is CN.

Another selected group of preferred compounds has formula I in which $R^4$ is

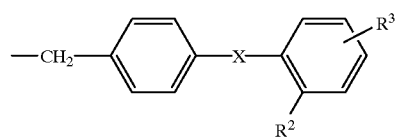

Another selected group of preferred compounds has formula I in which $R^4$ is cyanoalkyl or tetrazol-5-ylalkyl having 1–6 C atoms in the alkyl moiety in each case, or aralkyl having 7–11 C atoms which is unsubstituted or monosubstituted by Hal, $R^5$, COOH, COOA, CN, NO$_2$, NH$_2$, NH—CO—$R^5$, NH—SO$_2$-$R^5$ or tetrazol-5-yl.

The compounds of formula I and also the starting materials for their preparation are moreover prepared by methods known per se, such as those described in the literature (e.g. in the standard works like Houben-Weyl, Methoden der organischen Chemie (Methods of Organic Chemistry), Georg-Thieme-Verlag, Stuttgart, but especially U.S. Pat. No. 4,880,804), under conditions which are known and suitable for said reactions, it also being possible to make use of variants known per se, which are not mentioned in greater detail here.

If desired, the starting materials can also be formed in situ, so that they are not isolated from the reaction mixture but immediately reacted further to give the compounds of formula I.

The compounds of formula I can preferably be obtained by reacting compounds of formula II with compounds of formula III. Particularly the biphenyl derivatives of formula I (in which X is absent) are readily obtainable in this way.

In the compounds of formula II, E is preferably Cl, Br, I or an OH group which has been functionally modified to acquire reactivity, such as alkylsulphonyloxy having 1–6 C atoms (preferably methylsulphonyloxy) or arylsulphonyloxy having 6–10 C atoms (preferably phenyl- or p-tolyl-sulphonyloxy).

The reaction of II with III is conveniently carried out by first converting III to a salt by treatment with a base, e.g. with an alkali metal alcoholate such as CH$_3$ONa in an alcohol such as CH$_3$OH, or with an alkali metal hydride such as NaH in dimethylformamide (DMF), and then reacting said salt with II in an inert solvent, e.g. an amide such as DMF or dimethylacetamide, or a sulphoxide such as dimethyl sulphoxide (DMSO), conveniently at temperatures of between −20 and 100°, preferably of between 10 and 30°. Other suitable bases are alkali metal carbonates such as Na$_2$CO$_3$ or K$_2$CO$_3$, or alkali metal hydrogen carbonates such as NaHCO$_3$ or KHCO$_3$.

In the reaction of II with III, it is possible to obtain two or, in the case of III, $R^4$=H, three regioisomeric monosubstitution products, namely the corresponding 1H- and 3H-imidazo[4,5-c]pyridines in which the newly introduced substituent is in the 1, 3 or 5 position. It is also possible to obtain disubstitution products with substitution in the 1 and 3, 1 and 5 or 3 and 5 positions. The type and proportions of the products of formula I are extensively dependent on the proportions of the reactants II and III and on the reaction conditions. Thus, in the reaction of equimolar amounts of methyl 4'-bromomethylbiphenyl-2-carboxylate ("IIa") and 2-butyl-4-oxo-4,5-dihydro-1(or 3)H-imidazo[4,5-c]pyridine ("IIIa") in the presence of CH$_3$ONa in methanol, the products disubstituted in the 1 and 5 positions and in the 3 and 5 positions can be isolated; on the other hand, in the reaction of 4'-bromomethyl-2-cyanobiphenyl ("IIb") with IIIa in the presence of K$_2$CO$_3$ in DMF, the product monosubstituted-in the 3 position is obtained in very predominant proportions.

The compounds of formula I can also be obtained by the solvolysis, especially acid or alkaline hydrolysis, of compounds of formula IV. In IV, the radical $E^1$ is preferably Cl. The solvolysis of IV is also carried out particularly advantageously with silver acetate in acetic acid at temperatures of between 20° and the boiling point.

The compounds of formula I can also be obtained by the cyclization of compounds of formula V. This cyclization is conveniently carried out by heating with polyphosphoric acid, acetic acid or diglyme to temperatures of between about 80 and 180°, preferably of between 120 and 160°.

Acid amides of formula I (X=—NH—CO— or —CONH—) can also be obtained by reacting compounds of formula VI (or reactive derivatives thereof) with compounds of formula VII (or reactive derivatives thereof).

Suitable reactive derivatives of the carboxylic acids of formulae VI and VII ($x^1$ or $x^2$=COOH) are advantageously the corresponding chlorides, bromides or anhydrides. The reaction is conveniently carried out in the presence of an inert solvent, e.g. a halogenated hydrocarbon such as methylene chloride, chloroform, trichloroethene or 1,2-dichloroethane, or an ether such as tetrahydrofuran (THF) or dioxane, at temperatures of between 0 and 150°, preferably of between 20 and 80°. If acid halides are reacted, it is recommended to add a base, e.g. a tertiary amine such as triethylamine, pyridine or 4-dimethylamino-pyridine.

Ethers of formula I (X=—CH$_2$—O— or —O—CH$_2$—) can be obtained by reacting compounds of formulae VIII and IX (or reactive derivatives thereof). Suitable reactive derivatives of the phenols VIII and IX ($X^3$ or $X^4$=OH) are e.g. the corresponding alkali metal (e.g. Na, K) phenates, which can also be formed in situ from the phenol and a base (e.g. potassium carbonate). The reaction is conveniently carried out in the presence of an inert solvent, e.g. an amide such as DMF or a sulphoxide such as DMSO, at temperatures of between 0 and 150°, preferably of between 20 and 100°.

Additionally, one can liberate a compound of formula I from one of its functional derivatives by solvolysis (e.g., hydrolysis) or by hydrogenolysis.

Thus, it is possible by one of the methods described above to prepare a compound corresponding to formula I which, however, contains a tetrazol-5-yl group functionally modified (protected by a protective group) in 1 (or 2) position instead of containing a free tetrazol-5-yl group. Suitable protective groups are, e.g., triphenylmethyl (removable with HCl or formic acid in an inert solvent or solvent mixture, f.e. ether/dichloromethane/methanol);
2-cyanoethyl (removable with NaOH in aqueous THF); p-nitrobenzyl (removable with hydrogen on Raney nickel in ethanol).

Some of the starting materials, especially those of formula II, are known. If they are not known, they can be prepared by known methods analogously to known substances. Compounds of formula III are novel. Compounds of formula III ($R^4$=H,Y=O) can be obtained e.g. by reacting carboxylic acids of the formula $R^1$—COOH with compounds of formula X:

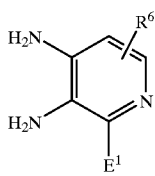

X in the presence of polyphosphoric acid, the group $E^1$ (preferably Cl) being hydrolyzed in the process.

Compounds of formula IV can be obtained for example by reacting compounds of the formula H—$R^7$ with compounds of formula II under the conditions indicated above for the reaction of II with III.

Compounds of formula V can be obtained e.g. by reacting compounds of formula XI:

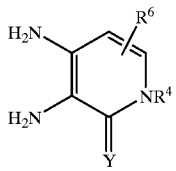

XI in which, however, one of the amino groups is protected by an amino-protecting group (e.g. benzyl, A—O—CO— or benzyloxycarbonyl), with compounds of formula II and subsequently cleaving the protecting group and reacting the products with acids of the formula $R^1$—COOH or functional derivatives thereof; they are not normally isolated, but are formed in situ in the last-mentioned reaction.

It is also possible to convert a compound of formula I to another compound of formula I by converting one or more of the radicals R, $R^2$ and/or $R^3$ to other radicals R, $R^2$ and/or $R^3$, e.g. by reducing nitro groups to amino groups (e.g. by hydrogenation on Raney nickel in an inert solvent such as methanol or ethanol), and/or functionally modifying free amino and/or hydroxyl groups, and/or freeing functionally modified amino and/or hydroxyl groups by solvolysis or hydrogenolysis, and/or replacing halogen atoms with CN groups (e.g. by reaction with copper(I) cyanide), and/or hydrolysing nitrile groups to COOH groups, or converting nitrile groups to tetrazolyl groups with hydrazoic acid derivatives, e.g. sodium azide in N-methylpyrrolidone or trimethyltin azide in toluene.

Thus, for example, free hydroxyl and/or amino groups can be acylated in conventional manner with an acid chloride or anhydride, or alkylated with a substituted or unsubstituted alkyl, alkenyl, alkynyl or aralkyl halide, conveniently in an inert solvent such as methylene chloride or THF, and/or in the presence of a base such as triethylamine or pyridine, at temperatures of between −60 and +30°. Of particular importance is the corresponding conversion of a radical R in which $R^4$=H to another radical R in which $R^4$ is other than H. This reaction is preferably carried out with an acid amide such as DMF, N-methylpyrrolidone, 1,3-dimethyl-2-oxo-hexahydropyrimidine or hexamethylphosphorotriamide, an alcohol such as methanol or tert-butanol, an ether such as THF, or a halogenated hydrocarbon such as methylene chloride, or mixtures thereof, as the solvent, and/or in the presence of an alkali metal alcoholate such as sodium methylate or potassium tert-butylate, an alkali metal hydride such as sodium or potassium hydride, an alkali metal carbonate such as sodium or potassium carbonate, an alkali metal bicarbonate such as sodium or potassium bicarbonate, or a tertiary amine such as triethylamine or ethyldiisopropylamine, at temperatures of between about −30 and 200, preferably of between 20 and 60°.

If desired, a functionally modified amino and/or hydroxyl group in a compound of formula I can be freed by solvolysis or hydrogenolysis using conventional methods. Thus, e.g., a compound of formula I containing an $NHCOR^5$ or AOOC group can be converted to the corresponding compound of formula I containing an $NH_2$ or HOOC group instead. AOOC groups can be saponified e.g. with NaOH or KOH in water, water/THF or water/dioxane, at temperatures of between 0 and 100°.

The reaction of nitriles of formula I ($R^2$=CN) with hydrazoic acid derivatives leads to tetrazoles of formula I ($R^2$=tetrazol-5-yl). It is preferable to use trialkyltin azides such as trimethyltin azide, in an inert solvent, e.g. an aromatic hydrocarbon such as toluene, at temperatures of between 20 and 150°, preferably of between 80 and 140°, or sodium azide in N-methylpyrrolidone at temperatures of between about 100 and 200°.

A base of formula I can be converted with an acid to the corresponding acid addition salt. Suitable acids for this reaction are especially those which yield physiologically acceptable salts. Thus it is possible to use inorganic acids, e.g. sulphuric acid, nitric acid, hydrohalic acids such as hydrochloric acid or hydrobromic acid, phosphoric acids such as orthophosphoric acid, and sulphamic acid, as well as organic acids, especially aliphatic, alicyclic, araliphatic, aromatic or heterocyclic monobasic or polybasic carboxylic, sulphonic or sulphuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethane-sulphonic acid, ethanedisulphonic acid, 2-hydroxyethanesulphonic acid, benzenesulphonic acid, p-toluenesulphonic acid, naphthalene-monosulphonic and disulphonic acids and lauryl-sulphuric acid. Salts with physiologically unacceptable acids, e.g. picrates, can be used for isolating and/or purifying the compounds of formula I.

On the other hand, compounds of formula I containing COOH or tetrazolyl groups can be converted with bases (e.g.,-sodium or potassium hydroxide or carbonate) to the corresponding metal salts, especially alkali metal or alkaline earth metal salts, or to the corresponding ammonium salts. The potassium salts of the tetrazolyl derivatives are particularly preferred.

The novel compounds of formula I and their physiologically acceptable salts can be used for the manufacture of pharmaceutical preparations by incorporation into a suitable dosage form together with at least one excipient or adjunct and, if desired, together with one or more other active ingredients. The resulting formulations can be used as drugs in human or veterinary medicine. Possible excipients are organic or inorganic substances which are suitable for enteral (e.g. oral or rectal) or parenteral administration or for administration in the form of an inhalation spray, and which do not react with the novel compounds, for example water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; lacquered tablets and capsules with coatings or shells resistant to gastric juices are of special interest. Suppositories are used for rectal administration and solutions, preferably oily or aqueous solutions, as well as suspensions, emulsions or implants, are used for parenteral administration. For administration as inhalation sprays, it is possible to use sprays containing the active ingredient either dissolved or suspended in a propellant mixture (e.g. fluorochlorohydrocarbons). It is convenient here to use the active ingredient in microni ed form, it being possible for one or more additional physiologically compatible solvents, e.g. ethanol, to be present. Inhalation solutions can be administered with the aid of conventional inhalers. The novel compounds can also be lyophilized and the resulting lyophilisates used e.g. for the manufacture of injection preparations. The indicated formulations can be sterilised and/or can contain adjuncts such as preservatives, stabilizers and/or wetting agents, emulsifiers, salts for influencing the osmotic pressure, buffer substances, colors and/or flavourings. If desired, they can also contain one or more other active ingredients, e.g. one or more vitamins, diuretics or antiphlogistics.

The substances according to the invention are normally administered analogously to other known, commercially available preparations, but in particular analogously to the compounds described in U.S. Pat. No. 4,880,804, preferably in dosages of between about 1 mg and 1 g, especially of between 50 and 500 mg per dosage unit. The daily dosage is preferably between about 0.1 and 500 mg/kg, especially between 1 and 100 mg/kg of body weight. However, the special dose for each particular patient depends on a very wide variety of factors, for example on the efficacy of the special compound used, age, body weight, general state of health, sex, diet, time and method of administration, rate of excretion, drug combination and severity of the particular disease to which the therapy is applied. Oral administration is preferred. The foregoing dosages apply to the use of the compounds of this invention for all of the purposes mentioned herein.

Above and below, all temperatures are given in ° C. In the following Examples, "conventional working-up" means: water is added if necessary, the pH is adjusted to between 2 and 10 if necessary, depending on the constitution of the end product, extraction is carried out with ethyl acetate or methylene chloride and the organic phase is separated off, dried over sodium sulfate, evaporated and purified by chromatography on silica gel and/or by crystallization. Rf values are determined by thin layer chromatography on silica gel using ethyl acetate as eluent unless specified other.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany P 41 10 019.0, filed Mar. 27, 1991, are hereby incorporated by reference.

EXAMPLES

Example 1

A solution of 0.4 g of Na in 20 ml of methanol is added dropwise over 15 min to a solution of 3.2 g of 2-butyl-4-oxo-4,5-dihydro-1(or 3)H-imidazo[4,5-c]pyridine ("IIIa") in 75 ml of methanol. The mixture is stirred at 20° for a further 30 min and evaporated, the residue is dissolved in 20 ml of DMF, and a solution of 5.2 g of methyl 4'-bromomethylbiphenyl-2-carboxylate (IIa) in 10 ml of DMF is added dropwise at 0°, with stirring. The mixture is stirred at 20° for 16 hours, evaporated, worked up in conventional manner and chromatographed on silica gel to give the following in succession using methyl tert-butyl ether/methanol (9.5:0.5 to 9:1):

2-butyl-3,5-bis(2'-methoxycarbonylbiphenyl-4-ylmethyl)-4,5-dihydro-4-oxo-3H-imidazo[4,5-c]pyridine, oil;

2-butyl-1-(2'-methoxycarbonylbiphenyl-4-ylmethyl)-4,5-dihydro-4-oxo-1H-imidazo[4,5-c]pyridine, m.p. 224°;

2-butyl-5-(2'-methoxycarbonylbiphenyl-4-ylmethyl)-4,5-dihydro-4-oxo-1(or 3)H-imidazo[4,5-c]pyridine, m.p. 151°;

2-butyl-3-(2'-methoxycarbonylbiphenyl-4-ylmethyl)-4,5-dihydro-4-oxo-3H-imidazo[4,5-c]pyridine, m.p. 186°;

2-butyl-1,5-bis(2'-methoxycarbonylbiphenyl-4-ylmethyl)-4,5-dihydro-4-oxo-1H-imidazo[4,5-c]pyridine, m.p. 68°.

Preparation of the starting material IIIa

A mixture of 16.2 g of 3,4-diamino-2chloro-pyridine, 14 ml of valeric acid and 300 g of polyphosphoric acid is heated at 100–140° for 8 hours and then at 170–180° for 5 hours, with stirring. It is cooled and poured on to ice, and sodium hydroxide solution is added to pH 9. After concentration and conventional working-up, IIIa is obtained: m.p. 285–290°.

The following are obtained analogously from IIa and 2-butyl-6-chloro-4-oxo-4,5-dihydro-1(or 3)H-imidazo[4,5-c]pyridine (m.p. 235–240°; obtainable from 3,4-diamino-2,6-dichloropyridine and valeric acid):

2-butyl-6-chloro-3,5-bis(2'methoxycarbonylbiphenyl-4-ylmethyl)-4,5-dihydro-4-oxo-3H-imidazo[4,5-c]pyridine;

2-butyl-6-chloro-1-(2'-methoxycarbonylbiphenyl-4-ylmethyl)-4,5-dihydro-4-oxo-1H-imidazo[4,5-c]pyridine;

2-butyl-6-chloro-5-(2'-methoxycarbonylbiphenyl-4-ylmethyl)-4,5-dihydro-4-oxo-1(or 3)H-imidazo[4,5-c]pyridine;

2-butyl-6-chloro-3-(2'-methoxycarbonylbiphenyl-4-ylmethyl)-4,5-dihydro-4-oxo-3H-imidazo[4,5-c]pyridine;

2-butyl-6-chloro-1,5-bis(2'-methoxycarbonylbiphenyl-4-ylmethyl)-4,5-dihydro-4-oxo-1H-imidazo[4,5-c]pyridine.

The following are obtained analogously from IIa and 2-butyl-4,5-dihydro-4-thioxo-1(or 3)H-imidazo-[4,5c]pyridine (obtainable from IIIa and Lawesson's reagent in toluene):

2-butyl-3,5-bis(2'-methoxycarbonylbiphenyl-4-ylmethyl)-4,5-dihydro-4-thioxo-3H-imidazo[4,5-c]pyridine;

2-butyl-1-(2'-methoxycarbonylbiphenyl-4-ylmethyl)-4,5-dihydro-4-thioxo-1H-imidazo[4,5-c]pyridine;

2-butyl-5-(2'-methoxycarbonylbiphenyl-4-ylmethyl)-4,5-dihydro-4-thioxo-1(or 3)H-imidazo[4,5-c]pyridine;

2-butyl-3-(2'-methoxycarbonylbiphenyl-4-ylmethyl)-4,5-dihydro-4-thioxo-3H-imidazo[4,5-c pyridine;

2-butyl-1,5-bis(2'-methoxycarbonylbiphenyl-4-ylmethyl)-4,5-dihydro-4-thioxo-1H-imidazo[4,5-c]pyridine.

The following are obtained analogously from IIa and 2-butyl-6-chloro-4,5-dihydro-4-thioxo-1(or 3)H-imidazo[4,5-c]pyridine:

2-butyl-6-chloro-3,5-bis(2'-methoxycarbonylbiphenyl-4-ylmethyl)-4,5-dihydro-4-thioxo-3H-imidazo[4,5-c] pyridine;

2-butyl-6-chloro-1-(2'-methoxycarbonylbiphenyl-4-ylmethyl)-4,5-dihydro-4-thioxo-1H-imidazo[4,5-c] pyridine;

2-butyl-6-chloro-5-(2'-methoxycarbonylbiphenyl-4-ylmethyl)-4,5-dihydro-4-thioxo-1(or 3)H-imidazo[4,5-c]-pyridine;

2-butyl-6-chloro-3-(2 '-methoxycarbonylbiphenyl-4-ylmethyl)-4,5-dihydro-4-thioxo-3H-imidazo(4,5-c] pyridine;

2-butyl-6-chloro-1,5-bis(2'-methoxycarbonylbiphenyl-4-ylmethyl)-4,5-dihydro-4-thioxo-1H-imidazo[4,5-c] pyridine;.

Example 2

A mixture of 0.7 g of IIIa, 0.5 g of $K_2CO_3$ and 40 ml of DMF is stirred at 20° for 10 min. A solution of 1 g of 4'-bromomethyl-2-cyanobiphenyl in 5 ml of DMF is added dropwise over 45 min, with stirring, and the mixture is stirred at 20° for a further 5 hours, evaporated and worked up in conventional manner to give the following after chromatography on silica gel (methylene chloride/methanol 98:2 to 9:1):

2-butyl-1-(2'-cyanobiphenyl-4-ylmethyl)-4,5-dihydro-4-oxo-1H-imidazo[4,5-c]pyridine;

2-butyl-3-(2'-cyanobiphenyl-4-ylmethyl)-4,5-dihydro-4-oxo-3H-imidazo[4-5-c]pyridine, m.p. 179° (main product);

2-butyl-5-(2'-cyanobiphenyl-4-ylmethyl)-4,5-dihydro-4-oxo-1(or 3)H-imidazo[4,5-c]pyridine;

2-butyl-1,5-bis(2 '-cyanobiphenyl-4-ylmethyl)-4,5-dihydro-4-oxo-1H-i-imidazo[4,5-c]pyridine;

2-butyl-3,5-bis(2'-cyanobiphenyl-4-ylmethyl)-4,5-dihydro-4-oxo-3H-imidazo[4,5-c]pyridine, m.p. 83°.

The following are obtained analogously with 2'-nitrobiphenyl-4-ylmethyl bromide:

2-butyl-1-(2'-nitrobiphenyl-4-ylmethyl)-4,5-dihydro-4-oxo-1H-imidazo[4,5-c]pyridine;

2-butyl-3-(2'-nitrobiphenyl-4-ylmethyl)-4,5-dihydro-4-oxo-3H-imidazo[4,5-c]pyridine;

2-butyl-5-(2'-nitrobiphenyl-4-ylmethyl)-4,5-dihydro-4-oxo-1(or 3)H-imidazo[4,5-c]pyridine;

2-butyl-1,5-bis(2'-nitrobiphenyl-4-ylmethyl)-4,5-dihydro-4-oxo-1H-imidazo[4,5-c]pyridine;

2-butyl-3,5-bis(2'-nitrobiphenyl-4-ylmethyl)-4,5-dihydro-4-oxo-3H-imidazo[4,5-c]pyridine.

Example 3

A mixture of 4 g of 2-butyl-3-(2'-cyanobiphenyl-4-ylmemethyl)-4-chloro-3H-imidazo[4,5-c]pyridine [obtainable by condensing 3,4-diamino-2-chloropyridine with valeric acid analogously to Example 4 to give 2-butyl-4-chloro-1(or -3)H-imidazo[4,5-c]pyridine (m.p. 65°) and reacting the latter with IIIa analogously to Example 2], 2 g of $CH_3COOAg$ and 40 ml of acetic acid is boiled for 16 hours. It is filtered and evaporated and the residue is worked up in conventional manner to give 2-butyl-3-(2'-cyanobiphenyl-4-ylmethyl)-4,5-dihydro-4-oxo-3H-imidazo[4,5-c]pyridine, m.p. 179°.

Example 4

A mixture of 1.02 g of valeric acid, 3.59 g of 4-amino-2-oxo-3-[2'-(tetrazol-5-yl)biphenyl-4-yl-methylamino]-1,2-dihydropyridine (obtainable by reacting 3-amino-4-benzylamino-1,2-dihydro-2-oxopyridine with 4-bromomethyl-2'-cyanobiphenyl to give 4-benzylamino-3-(2'-cyanobiphenyl-4-ylmethylamino)-1,2-dihydro-2-oxopyridine, reacting the latter with trimethyltin azide according to Example 13 to give 4-benzylamino-3-[2'-(tetrazol-5-yl)biphenyl-4-ylmethylamino-1,2-dihydro-2-oxopyridine, and removing the benzyl group by hydrogenolysis] and 50 g of polyphosphoric acid is heated at 140° for 5 hours. 4-amino-2-oxo-3-[N-2'-(tetrazol-5-yl) biphenyl-4-ylmethyl-N-valerylamino]-1,2-dihydro-pyridine and 2-oxo-3-[2'-(tetrazol-5-yl)biphenyl-4-ylmethylamino]-4-valerylamino-1,2-dihydropyridine are formed in situ as intermediates. The mixture is cooled, poured on to ice, rendered alkaline with sodium hydroxide solution and worked up in conventional manner to give 2-butyl-4-oxo-3-[2'-(tetrazol-5-yl)biphenyl-4-ylmethyl]- 4,5-dihydro-3H-imidazo[4,5-c]pyridine, m.p. 167°.

Example 5

A mixture of 1 g of 3-p-aminobenzyl-2-butyl-4,5-dihydro-4-oxo-3H-imidazo[4,5-c]pyridine, 0.6 g of phthalic anhydride and 40 ml of $CHCl_3$ is stirred at 20° for 16 hours. The precipitate of 2-butyl-3-[4-(2-carboxybenzamido) benzyl]-4,5-dihydro-4-oxo-3H-imidazo[4,5-c]pyridine is filtered off.

The following are obtained analogously from the corresponding aminobenzyl compounds:

2-butyl-1-[4-(2-carboxybenzamido)benzyl]-4,5-dihydro-4-oxo-1H-imidazo[4,5-c ]pyridine;

2-butyl-5-[4-(2-carboxybenzamido)benzyl]-4,5-dihydro-4-oxo-1(or 3)H-imidazo[4,5-c]pyridine;

2-butyl-3,5-bis[4-(2-carboxybenzamido)benzyl]-4,5-dihydro-4-oxo-3H-imidazo[4,5-c]pyridine.

Preparation of the starting material (a) 3 g of IIIa are dissolved in 75 ml of methanol, and a solution of 0.4 g of Na in 10 ml of methanol is added dropwise at 20°, with stirring. The mixture is stirred for a further 45 min and evaporated, the residue is dissolved in 30 ml of DMF, the solution is cooled to 0°, a solution of 3.7 g of p-nitrobenzyl bromide is added at this temperature and the mixture is stirred at 20° for 16 hours. It is evaporated and worked up in conventional manner to give 2-butyl-3,5-bis(p-nitrobenzyl)-4,5-dihydro-4-oxo-3H-imidazo[4,5-c]pyridine (m.p. 142–143°), 2-butyl-1-p-nitrobenzyl-4,5-dihydro-4-oxo-1H-imidazo[4,5-c] pyridine, 2-butyl-3-p-nitrobenzyl-4,5-dihydro-4-oxo-3H-imidazo[4,5-c]pyridine (m.p. 193–194°) and 2-butyl-5-p-nitrobenzyl-4,5-dihydro-4-oxo-1(or 3)H-imidazo[4,5-c] pyridine ($M^+310$) after chromatographic separation (silica gel; $CH_2Cl_2/CH_3OH$ 95:5).

(b) A solution of 1.7 g of 2-butyl-3-p-nitrobenzyl-4,5-dihydro-4-oxo-3H-imidazo[4,5-c]pyridine in 50 ml of methanol is hydrogenated at 20° on 1.7 g of Raney Ni until the absorption of $H_2$ has ceased. The mixture is filtered and evaporated to give 3-p-aminobenzyl-2-butyl-4,5-dihydro-4-oxo-3H-imidazo[4,5-c]pyridine.

The following are obtained analogously by hydrogenation of the corresponding nitro compounds:

1-p-aminobenzyl-2-butyl-4,5-dihydro-4-oxo-1H-imidazo[4,5-c]pyridine;

5-p-aminobenzyl-2-butyl-4,5-dihydro-4-oxo-1(or 3)H-imidazo[4,5-c]pyridine;

3,5-bis(p-aminobenzyl)-2-butyl-4,5-dihydro-4-oxo-3H-imidazo[4,5-c]pyridine.

Example 6

A mixture of 2.96 g of 1-p-aminobenzyl-2-butyl-4,5-dihydro-4-oxo-1H-imidazo[4,5-c]pyridine, 3 ml of triethylamine, 0.5 g of 4-dimethylaminopyridine and 120 ml of $CH_2Cl_2$ is cooled to 5° and a solution of 2.88 g of o-trifluoromethanesulphonamidobenzoyl chloride in 20 ml of $CH_2Cl_2$ is added dropwise. The mixture is stirred at 20° for a further 16 hours, evaporated and worked up in conventional manner to give 2-butyl-4-oxo-1-[4-(2-trifluoromethanesulphonamidobenzamido)benzyl]-4,5-dihydro-1H-imidazo[4,5-c]pyridine.

The following are obtained analogously from the corresponding p-aminobenzyl derivatives:
2-butyl-4-oxo-3-[4-(2-trifluoromethanesulphonamidobenzamido)benzyl]-4,5-dihydro-3H-imidazo[4,5-c]pyridine;
2-butyl-4-oxo-5-[4-(2-trifluoromethanesulphonamidobenzamido)benzyl]-4,5-dihydro-1(or 3)H-imidazo[4,5-c]pyridine;
2-butyl-4-oxo-3,5-bis[4-(2-trifluoromethanesulphonamidobenzamido)benzyl]-4,5-dihydro-3H-imidazo[4,5-c]pyridine.

Example 7

A mixture of 3.25 g of 2-butyl-3-p-carboxybenzyl-4,5-dihydro-4-oxo-3H-imidazo[4,5-c]pyridine, 12 g of thionyl chloride and 35 ml of $CHCl_3$ is boiled for 6 hours and evaporated. The crude acid chloride obtained is freed by multiple dissolution in toluene and evaporation of thionyl chloride residues and dissolved in 50 ml of THF. This solution is added dropwise to a solution of 1.7 g of anthranilic acid and 0.8 g of NaOH in 100 ml of water and the mixture is stirred for 24 hours and acidified to pH 5 with hydrochloric acid. After conventional working-up, 2-butyl-3-[4-(2-carboxyanilinocarbonyl)benzyl]-4,5-dihydro-4-oxo-3H-imidazo[4,5-c]pyridine is obtained.

The following are obtained analogously:
2-butyl-1-[4-(2-carboxyanilinocarbonyl)benzyl]-4,5-dihydro-4-oxo-1H-imidazo[4,5-c]pyridine;
2-butyl-5-[4-(2-carboxyanilinocarbonyl)benzyl]-4,5-dihydro-4-oxo-1(or 3)H-imidazo[4,5-c]pyridine;
2-butyl-1,5-bis[4-(2-carboxyanilinocarbonyl)benzyl]-4,5-dihydro-4-oxo-1H-imidazo[4,5-c]pyridine;
2-butyl-3,5-bis[4-(2-carboxyanilinocarbonyl)benzyl]-4,5-dihydro-4-oxo-3H-imidazo[4,5-c]pyridine.
Preparation of the starting materials
(a) Analogously to Example 1, IIIa is reacted with p-bromomethylbenzonitrile to give the following after chromatography on silica gel (methyl tert-butyl ether/methanol:
2-butyl-1-p-cyanobenzyl-1H-imidazo[4,5-c]pyridine;
2-butyl-3-p-cyanobenzyl-3H-imidazo[4, 5-c]pyridine;
2-butyl-5-p-cyanobenzyl-1(or 3)H-imidazo[4,5-c]pyridine;
2-butyl-1,5-bis(p-cyanobenzyl)-4,5-dihydro-4-oxo-1H-imidazo[4,5-c]pyridine;
2-butyl-3,5-bis(p-cyanobenzyl)-4,5-dihydro-4-oxo-3H-imidazo[4,5-c]pyridine.
(b) A mixture of 1 g of 2-butyl-3-p-cyanobenzyl-4,5-dihydro-4-oxo-3H-imidazo[4,5-c]pyridine, 0.7 g of KOH, 20 ml of ethanol and 5 ml of water is boiled for 24 hours, with stirring, and evaporated, the residue is dissolved in water and the solution is acidified with hydrochloric acid. The precipitate of 2-butyl-3-p-carboxybenzyl-4,5-dihydro-4-oxo-3H-imidazo[4,5-c]pyridine is filtered off and washed with water.
The following are obtained analogously by hydrolysis of the nitrites described under (a):
2-butyl-1-p-carboxybenzyl-4,5-dihydro-4-oxo-1H-imidazo-[4,5-c]pyridine;
2-butyl-5-p-carboxybenzyl-4,5-dihydro-4-oxo-1(or 3)H-imidazo[4,5-c]pyridine;
2-butyl-1,5-bis(p-carboxybenzyl)-4,5-dihydro-4-oxo-1H-imidazo[4,5-c]pyridine;
2-butyl-3,5-bis(p-carboxybenzyl)-4,5-dihydro-4-oxo-3H-imidazo[4,5-c]pyridine.

Example 8

A mixture of 1.19 g of o-cyanophenol, 0.75 g of $K_2CO_3$ and 10 ml of DMF is stirred for 0.5 hour. A solution of 3.76 g of 3-p-bromomethylbenzyl-2-butyl-4,5-dihydro-4-oxo-3H-imidazo[4,5-c]pyridine (obtainable by reacting IIIb with p-benzyloxymethylbenzyl bromide to give 3-p-benzyloxymethylbenzyl-2-butyl-4,5-dihydro-4-oxo-3H-imidazo[4,5-c]pyridine, subjecting the latter to hydrogenolysis to give the 3-p-hydroxymethylbenzyl compound and reacting the latter with $PBr_3$) in 20 ml of DMF is added dropwise and the mixture is heated at 90° for 8 hours and evaporated to give 2-butyl-3-(4-o-cyanophenoxymethylbenzyl)-4,5-dihydro-4-oxo-3H-imidazo[4,5-c]pyridine after conventional working-up.

Example 9

A mixture of 2.97 g of 2-butyl-3-p-hydroxybenzyl--4,5-dihydro-4-oxo-3H-imidazo[4,5-c]pyridine (obtainable from IIIa and p-hydroxybenzyl bromide), 0.5 g of $CH_3ONa$ and 40 ml of DMSO is stirred for 0.5 hour. A solution of 2.2 g of o-cyanobenzyl bromide in 15 ml of DMSO is added dropwise and the mixture is stirred at 20° for 16 hours and evaporated to give 2-butyl-3-(4-o-cyanobenzyloxybenzyl)-4,5-dihydro-4-oxo-3H-imidazo[4,5-c]pyridine after conventional working-up.

Example 10

A mixture of 1 g of 2-butyl-1-(2'-methoxycarbonylbiphenyl-4-ylmethyl)-4,5-dihydro-4-oxo-1H-imidazo[4,5-c]pyridine, 12 ml of 2 N aqueous NaOH solution and 43 ml of ethanol is boiled for 2 hours and then evaporated. Acidification to pH 3 with HCl gives 2-butyl-1-(2'-carboxybiphenyl-4-ylmethyl)-4,5-dihydro-4-oxo-1H-imidazo[4,5-c]pyridine, which is filtered off, washed with water and dried: m.p. 286°.

The following are obtained analogously by saponification of the corresponding methyl esters:
2-butyl-3-(2'-carboxybiphenyl-4-ylmethyl)-4,5-dihydro-4-oxo-3H-imidazo[4,5-c]pyridine, m.p. 275°;
2-butyl-5-(2'-carboxybiphenyl-4-ylmethyl)-4,5-dihydro-4-oxo-1(or 3)H-imidazo[4,5-c]pyridine;
2-butyl-1,5-bis(2'-carboxybiphenyl-4-ylmethyl)-4,5-dihydro-4-oxo-1H-imidazo[4,5-c]pyridine, m.p. 137°;
2-butyl-3,5-bis(2'-carboxybiphenyl-4-ylmethyl)-4,5-dihydro-4-oxo-3H-imidazo[4,5-c]pyridine, m.p. 165°.

Example 11

A solution of 0.79 g of chloroacetonitrile in 5 ml of DMF is added dropwise at 20°, with stirring, to a solution of 3.82 g of 2-butyl-3-(2'-cyanobiphenyl-4-ylmethyl)-4,5-dihydro-4-oxo-3H-imidazo[4,5-c]pyridine and 1.17 g of potassium tert-butylate in 20 ml of DMF. The mixture is stirred at 20° for a further 30 min and poured on to ice, hydrochloric acid is added to pH 6 and the mixture is worked up in conventional manner to give 2-butyl-3-(2'-cyanobiphenyl-4-ylmethyl)-5-cyanomethyl-4,5-dihydro-4-oxo-3H-imidazo [4,5-c]pyridine, m.p. 64°.

The following 2-butyl-3-(2'-cyanobiphenyl-4-yl-methyl)-4,5-dihydro-4-oxo-3H-imidazo[4,5-c]pyridines are obtained analogously:

| | |
|---|---|
| with methyl iodide: | 5-methyl-, m.p. 107° |
| with ethyl iodide: | 5-ethyl- |
| with isopropyl iodide: | 5-isopropyl- |
| with butyl bromide: | 5-butyl- |
| with tert-butyl bromide: | 5-tert-butyl- |
| with pentafluoroethyl iodide: | 5-pentafluoroethyl- |
| with 3,3,3-trifluoropropyl iodide: | 5-(3,3,3-trifluoro-propyl)- |
| with 2,2,2-trifluoroethyl iodide: | 5-(2,2,2-trifluoroethyl)-, oil, Rf 0.3 (ethyl acetate/hexane 9:1) |
| with 3-bromopropionitrile: | 5-(2-cyanoethyl)- |
| with 4-bromobutyronitrile: | 5-(3-cyanopropyl)- |
| with methyl bromoacetate: | 5-methoxycarbonyl methyl-, m.p. 82° |
| with ethyl 3-bromopropionate: | 5-(2-ethoxycarbonyl ethyl)- |
| with allyl bromide: | 5-allyl- |
| with propargyl bromide: | 5-propargyl- |
| with benzyl bromide: | 5-benzyl-, m.p. 119° |
| with o-fluorobenzyl bromide: | 5-(o-fluorobenzyl)-, oil, Rf 0.56 (ethyl acetate/hexane 1:1) |
| with m-fluorobenzyl bromide: | 5-(m-fluorobenzyl)-, oil, Rf 0.54 (ethyl acetate/hexane 1:1) |
| with p-fluorobenzyl bromide: | 5-(p-fluorobenzyl)-, m.p. 156° |
| with o-chlorobenzyl bromide: | 5-(o-chlorobenzyl)-, m.p. 130° |
| with m-chlorobenzyl bromide: | 5-(m-chlorobenzyl)-, m.p. 127° |
| with p-chlorobenzyl bromide: | 5-(p-chlorobenzyl)-, m.p. 124° |
| with o-bromobenzyl bromide: | 5-(o-bromobenzyl)-, m.p. 142° |
| with m-bromobenzyl bromide: | 5-(m-bromobenzyl)- |
| with p-bromobenzyl bromide: | 5-(p-bromobenzyl)-, m.p. 98° |
| with o-trifluoromethylbenzyl bromide: | 5-(o-trifluoromethyl benzyl)-, m.p. 105° |
| with m-trifluoromethylbenzyl bromide: | 5-(m-trifluoromethyl benzyl)- |
| with p-trifluoromethylbenzyl bromide: | 5-(p-trifluoromethyl benzyl)- |
| with o-methoxycarbonylbenzyl bromide: | 5-(o-methoxycarbonyl benzyl)-, m.p. 59° |
| with m-methoxycarbonylbenzyl bromide: | 5-(m-methoxycarbonyl benzyl)- |
| with p-methoxycarbonylbenzyl bromide: | 5-(p-methoxycarbonyl benzyl)-, m.p. 120° |
| with o-cyanobenzyl bromide: | 5-(o-cyanobenzyl)-, m.p. 65° |
| with m-cyanobenzyl bromide: | 5-(m-cyanobenzyl)-, m.p. 140° |
| with o-ethoxycarbonylbenzyl bromide: | 5-(o-ethoxycarbonyl-benzyl)- |
| with m-ethoxycarbonylbenzyl bromide: | 5-(o-ethoxycarbonyl-benzyl)- |
| with p-ethoxycarbonylbenzyl bromide: | 5-(p-ethoxycarbonyl-benzyl)- |
| with p-cyanobenzyl bromide: | 5-(p-cyanobenzyl)- |
| with o-nitrobenzyl chloride: | 5-(o-nitrobenzyl)-, m.p. 149° |
| with m-nitrobenzyl chloride: | 5-(m-nitrobenzyl)- |
| with p-nitrobenzyl chloride: | 5-(p-nitrobenzyl)-, m.p. 142° |
| with o-trifluoroacetamido-benzyl bromide: | 5-(o-trifluoroacet amidobenzyl)- |
| with m-trifluoroacetamido-benzyl bromide: | 5-(m-trifluoroacet amidobenzyl)- |
| with p-trifluoroacetamido-benzyl bromide: | 5-(p-trifluoroacet amidobenzyl)- |
| with o-trifluoromethylsulphon-amidobenzyl bromide: | 5-(o-trifluoromethyl sulphonamidobenzyl)- |
| with m-trifluoromethylsulphon-amidobenzyl bromide: | 5-(m-trifluoromethyl sulphonamidobenzyl)- |
| with p-trifluoromethylsulphon-amidobenzyl bromide: | 5-(p-trifluoromethyl sulphonamidobenzyl)- |
| with 2,6-dichlorobenzyl bromide: | 5-(2,6-dichlorobenzyl)-, m.p. 178° |
| with 2-fluoro-4-nitrobenzyl bromide: | 5-(2-fluoro-4-nitrobenzyl)-, m.p. 193° |
| with 2-chloro-4-nitrobenzyl bromide: | 5-(2-chloro-4-nitrobenzyl)- m.p. 206°. |

Example 12

A mixture of 800 mg of 2-butyl-3-(2'-cyano-biphenyl-4-ylmethyl)-4,5-dihydro-4-oxo-3H-imidazo[4,5-c]-pyridine, 515 mg of trimethyltin azide and 20 ml of toluene is boiled for 96 hours and evaporated. Chromatography of the residue (silica gel; methylene chloride/-methanol 9:1, then 85:15 and 80:20) yields 2-butyl-4,5-dihydro-4-oxo-3-[2'-(tetrazol-5-yl)biphenyl-4-ylmethyl]- 3H-imidazo[4,5-c]pyridine, m.p.167°. The corresponding K salt is prepared therefrom in conventional manner.

The following are obtained analogously from the corresponding cyano compounds:
2-butyl-4,5-dihydro-4-oxo-1-[2'-tetrazol-5-yl)biphenyl-4-ylmethyl]-1H-imidazo[4,5-c]pyridine;
2-butyl-4,5-dihydro-4-oxo-5-[2'-tetrazol-5-yl)biphenyl-4-ylmethyl]-1(or 3)H-imidazo[4,5-c]pyridine;
2-butyl-4,5-dihydro-4-oxo-1,5-bis[2'-(tetrazol-5-yl)biphenyl-4-ylmethyl]-1H-imidazo[4,5-c]pyridine, m.p. >300°
2-butyl-4,5-dihydro-4-oxo-3,5-bis[2'-(tetrazol-5-yl)biphenyl-4-ylmethyl]-3H-imidazo[4,5-c]pyridine;
2-butyl-4,5-dihydro-4-oxo-3-[4-o-(tetrazol-5-yl)phenoxy-methylbenzyl]-3H-imidazo[4,5-c]pyridine;
2-butyl-4,5-dihydro-4-oxo-3-[4-o-(tetrazol-5-yl)-benzyloxybenzyl]-3H-imidazo[4,5-c]pyridine.

The following 2-butyl-4,5-dihydro-4-oxo-3-[2'-(tetrazol-5-yl)biphenyl-4-ylmethyl]-3H-imidazo[4,5-c]-pyridines are obtained analogously from the compounds described in Example 11:
5-(tetrazol-5-yl)methyl-, m.p. >300°; Rf 0.07 (ethyl acetate/methanol 1
5-methyl-
5-ethyl-
5-isopropyl-
5-butyl-
5-tert-butyl-
5-pentafluoroethyl-
5-(3,3,3-trifluoropropyl)-
5-[2-(tetrazol-5-yl)ethyl]-
5-[3-(tetrazol-5-yl)propyl]-
5-methoxycarbonylmethyl-
5-(2-ethoxycarbonylethyl) -
5-allyl-
5-propargyl-
5-benzyl-, m.p. 130°; potassium salt, m.p. 250°
5-(o-fluorobenzyl)-, m.p. 118°
5-(m-fluorobenzyl)-, m.p. 182°(dec.)
5-(p-fluorobenzyl)-, m.p. 135°
5-(o-chlorobenzyl)-, m.p. 123°
5-(m-chlorobenzyl)-, m.p. 126°
5-(p-chlorobenzyl)-, m.p. 145°
5-(o-bromobenzyl)-, m.p. 173°
5-(m-bromobenzyl)-
5-(p-bromobenzyl)-
5-(p-methylbenzyl)-
5-(o-trifluoromethylbenzyl)-
5-(m-trifluoromethylbenzyl)-
5-(p-trifluoromethylbenzyl)-
5-(o-methoxycarbonylbenzyl)-, m.p. 124°
5-(m-methoxycarbonylbenzyl)-
5-(p-methoxycarbonylbenzyl)-, m.p. 188°
5-(o-ethoxycarbonylbenzyl)-
5-(m-ethoxycarbonylbenzyl)-
5-(p-ethoxycarbonylbenzyl)-
5-[o-(tetrazol-5-yl)benzyl]-, m p. 243°
5-[m-(tetrazol-5-yl)benzyl]-, m.p. >300°
5-[p-(tetrazol-5-yl)benzyl]-
5-(o-nitrobenzyl)-, m.p. 189°
5-(m-nitrobenzyl)-
5-(p-nitrobenzyl)-, m.p. >300°
5-(o-trifluoroacetamidobenzyl)-

5-(m-trifluoroacetamidobenzyl)-
5-(p-trifluoroacetamidobenzyl)-
5-(o-trifluoromethylsulphonamidobenzyl)-
5-(m-trifluoromethylsulphonamidobenzyl)-
5-(p-trifluoromethylsulphonamidobenzyl)-
5-(2-fluoro-4-nitro-benzyl)-, m.p. 198°
5-(2-chloro-4-nitro-benzyl)-, m.p. 144°

Example 13

A solution of 1 g of 2-butyl-3-(2'-nitrobiphenyl-4-ylmethyl)-4,5-dihydro-4-oxo-3H-imidazo[4,5-c]pyridine in 30 ml of ethanol is hydrogenated at 20° on 1 g of Raney Ni until the absorption of $H_2$ has ceased. The mixture is filtered and evaporated to give 3-(2'-aminobiphenyl-4-ylmethyl)-2-butyl-4,5-dihydro-4-oxo-3H-imidazo[4,5-c]pyridine.

The following are obtained analogously by hydrogenation of the corresponding nitro compounds:
1-(2'-aminobiphenyl-4-ylmethyl)-2-butyl-4,5-dihydro-4-oxo-1H-imidazo[4,5-c]pyridine;
5-(2'-aminobiphenyl-4-ylmethyl)-2-butyl-4,5-dihydro-4-oxo-1(or 3)H-imidazo[4,5-c]pyridine;
1,5-bis(2'-aminobiphenyl-4-ylmethyl)-2-butyl-4,5-dihydro-4-oxo-1H-imidazo[4,5-c]pyridine;
3,5-bis(2'-aminobiphenyl-4-ylmethyl)-2-butyl-4,5-dihydro-4-oxo-3H-imidazo[4,5-c]pyridine;
5-(o-aminobenzyl)-2-butyl-3-(2'-cyanobiphenyl-4-ylmethyl)-4,5-dihydro-4-oxo-3H-imidazo[4,5-c]pyridine;
5-(m-aminobenzyl)-2-butyl-3-(2'-cyanobiphenyl-4-ylmethyl)-4,5-dihydro-4-oxo-3H-imidazo[4,5-c]pyridine;
5-(p-aminobenzyl)-2-butyl-3-(2'cyanobiphenyl-4-ylmethyl)-4,5-dihydro-4-oxo-3H-imidazo[4,5-c ]pyridine
5-(o-aminobenzyl)-2-butyl-4,5-dihydro-4-oxo-3-[2'-(tetrazol-5-yl)-biphenyl4-ylmethyl]-3H-imidazo[4,5-c]pyridine, m.p. 223°
5-(m-aminobenzyl)-2-butyl-4,5-dihydro-4-oxo-3-[2'(tetrazol-5-yl)-biphenyl4-ylmethyl]-3H-imidazo[4,5-c]pyridine
5-(p-aminobenzyl)-2-butyl-4,5-dihydro-4-oxo-3-[2'-(tetrazol-5-yl)-biphenyl-4-ylmethyl]-3H-imidazo[4,5-c]pyridine.

Example 14

A solution of 2.82 g of trifluoromethanesulphonic anhydride in 10 ml of $CH_2Cl_2$ is added dropwise to a solution of 3.72 g of 3-(2'-aminobiphenyl-4-ylmethyl)-2-butyl-4,5-dihydro-4-oxo-3H-imidazo[4,5-c]pyridine and 1.01 g of triethylamine in 30 ml of $CH_2Cl_2$ at −50 to −60°. The mixture is left to warm up to 20° and poured into dilute acetic acid to give 2-butyl-4,5-dihydro-4-oxo-3-(2'-trifluoromethanesulphonamidobiphenyl-4-ylmethyl)-3H-imidazo[4,5-c] pyridine after conventional working-up.

The following are obtained analogously from the corresponding amino compounds:
2-butyl-4,5-dihydro-4-oxo-1-(2'-trifluoromethanesulphonamidobiphenyl-4-ylmethyl)-1H-imidazo[4,5-c]-pyridine;
2-butyl-4,5-dihydro-4-oxo-5-(2'-trifluoromethanesulphonamidobiphenyl-4-ylmethyl)-1(or 3)H-imidazo[4,5-c]-pyridine;
2-butyl-4,5-dihydro-4-oxo-1,5-bis(2'-trifluoromethanesulphonamidobiphenyl-4-ylmethyl)-1H-imidazo[4,5-c]-pyridine;
2-butyl-4,5-dihydro-4-oxo-3,5-bis(2'-trifluoromethanesulphonamidobiphenyl-4-ylmethyl)-3H-imidazo[4,5-c]-pyridine.

Example 15 a) In analogy to Example 2, 2-butyl-3-[2'-(1(or 2)-triphenylmethyl-tetrazol-5-yl)-biphenyl-4-ylmethyl]-4,5-dihydro-4-oxo-3H-imidazo[4,5-c]pyridine, m.p.127°, is obtained from IIIa and 4-bromomethyl-2'-(1(or 2)-triphenylmethyl-tetrazol-5-yl)-biphenyl.

b) In analogy to Example 11, 5-benzyl-2-butyl-3-[2'-(1(or 2)-triphenylmethyl-tetrazol-5-yl)-biphenyl-4-ylmethyl]-4,5-dihydro-4-oxo-3H-imidazo[4,5-c]pyridine is obtained therefrom with benzyl bromide.

c) A solution of HCl in diethyl ether (4ml) is added to a solution of 1 g of the product obtained according to b) in 4ml of dichloromethane and 4 ml of methanol. The mixture is stirred for 3 hours at 20°, evaporated and worked up in conventional manner. After chromatographical separation of the triphenylcarbinol formed, 5-benzyl-2-butyl-4,5-dihydro-4-oxo-3-[2'-(tetrazol-5-yl)-biphenyl-4-ylmethyl]-3H-imidazo[4,5-c]pyridine is obtained; m.p. 130°. Potassium salt, m.p. 250°.

Example 16

One normal aqueous NaOH solution (3ml) is added to a solution of 573mg of 2-butyl-4,5-dihydro-5-p-methoxycarbonylbenzyl-4-oxo-3-[2'-(tetrazol-5-yl)-biphenyl-4-ylmethyl]-3H-imidazo[4,5-c]pyridine in 17 ml of THF and 6 ml of methanol., The mixture is stirred for 5 hours at 20°, acidified with HCl and worked up in conventional manner. 2-Butyl-5-p-carboxybenzyl-4,5-dihydro-4-oxo-3-[2'-(tetrazol-5-yl)-biphenyl-4-ylmethyl]-3H-imidazo[4,5-c]pyridine is obtained; m.p. >300°; Rf 0.26 (ethyl acetate/methanol 1:1).

Analogously, the following 2-butyl-4,5-dihydro-4-oxo-3-[2'- (tetrazol-5-yl)-biphenyl-4-ylmethyl]-3H-imidazo[4,5-c] pyridines are obtained by saponification of the corresponding methyl esters:
5-o-carboxybenzyl-, m.p. 211°.
5m-carboxybenzyl-.

Example 17 a) A mixture of 1450 ml of DMF, 219.7 g of 2-butyl-3-(2'-cyano-biphenyl-4-ylmethyl)-4,5-dihydro-4-oxo-5-(o-ethoxycarbonyl-benzyl)-3H-imidazo[4,5-c]pyridine, 166.5 g of triethylammonium chloride and 78.6 g of sodium azide is heated to 120° for 22 hours. After cooling, the mixture is worked up conventionally with ethyl acetate and water, the crude product is purified several times by suspending it in ethanol and filtering, and 2-butyl-4,5-dihydro-4-oxo-3-[2'-(tetrazol-5-yl)-biphenyl-4-ylmethyl]-5-(o-ethoxycarbonyl-benzyl)-3H-imidazo[4,5-c]-pyridine is obtained; m.p. 203–20°.

b) A solution of 16.3 g of K-tert.-butylate in 160 ml of ethanol is added slowly at 5° to a suspension of 85.5 g of the preceding tetrazole in 735 ml of ethanol with stirring. Stirring is continued for 2 hours at 5° which gives a clear solution. This is filtered and the filtrate is cooled to yield crystals of the potassium salt of 2-butyl-4,5-dihydro-4-oxo-3-[2'-(tetrazol-5-yl)-biphenyl-4-ylmethyl]-5-(o-ethoxycarbonyl-benzyl)-3H-imidazo[4,5-c]pyridine. No m.p. up to 3000°.

The following Examples relate to pharmaceutical formulations containing active ingredients of formula I or their salts.

Example A: Tablets and coated tablets

Tablets of the following composition are produced by compression in conventional manner and, where required, are provided with a conventional sucrose-based coating:

| | |
|---|---|
| 2-Butyl-3-(2'-cyanobiphenyl-4-ylmethyl)-4,5-dihydro-4-oxo-3H-imidazo[4,5-c]pyridine | 100 mg |
| Microcrystalline cellulose | 278.8 mg |
| Lactose | 110 mg |
| Maize starch | 11 mg |
| Magnesium stearate | 5 mg |
| Finely divided silicon dioxide | 0.2 mg |
| Example B: Hard gelatin capsules | |
| Conventional two-part hard gelatin capsules are each filled with | |
| Active ingredient of formula I | 100 mg |
| Lactose | 150 mg |
| Cellulose | 50 mg |
| Magnesium stearate | 6 mg |

Example C: Soft gelatin capsules

Conventional soft gelatin capsules are filled with a mixture of 50 mg of active ingredient and 250 mg of olive oil in each case.

Example D: Ampoules

A solution of 200 g of active ingredient in 2 kg of propane-1,2-diol is made up to 10 l with water and filled into ampoules so that each ampoule contains 20 mg of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An imidazopyridine derivative of formula I:

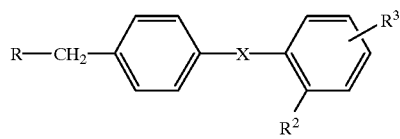

wherein

R is

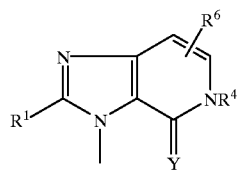

R$^1$ is A, alkenyl or alkynyl each having up to 6 C atoms, R$^2$ is COOH, COOA, CN, NO$_2$, NH$_2$, NHCOR$^5$, NHSO$_2$R$^5$ or tetrazol-5-yl, R$^3$ is H, R$^4$ is aralkyl having 7–11 C atoms which is unsubstituted or mono- or disubstituted by Hal, R$^5$, COOH, COOA, CN, NO$_2$, NH$_2$, NHA, N(A)$_2$, NHCOR$^5$, NHCOOA, NHSO$_2$R$^5$, OH, OA or tetrazol-5-yl, or

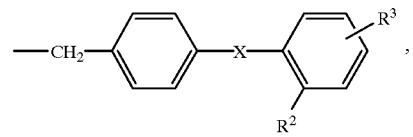

R$^5$ is alkyl having 1–4 C atoms, in which one or more H atoms can also be replaced with F, R$^6$ is H, X is a bond, Y is O, A is alkyl having 1–6 C atoms and Hal is F or Cl, or a physiologically acceptable salt thereof.

2. A compound according to claim 1, wherein

R$^1$ is A,

R$^2$ is COOH, COOA, CN or tetrazol-5-yl, and

R$^4$ is phenyl-alkyl having 7–11 C atoms which is unsubstituted or mono- or disubstituted in the phenyl ring by Hal, R$^5$, COOH, COOA, CN, NO$_2$, NH$_2$ and/or tetrazol-5-yl, or a physiologically acceptable salt thereof.

3. A compound according to claim 2, wherein R$^2$ is tetrazol-5-yl.

4. A compound according to claim 2 wherein R$^4$ is a benzyl group which is unsubstituted or substituted by one or two of F, Cl, COOH, COOA, CN, NO$_2$, NH$_2$ and tetrazol-5-yl.

5. A compound according to claim 1 which is selected from the group consisting of 2-butyl-4,5-dihydro-4-oxo-3-[2'-(tetrazol-5-yl)-biphenyl-4-yl-methyl]-3H-imidazo[4,5-c]pyridine or a potassium salt thereof, and 5-benzyl-2-butyl-4,5-dihydro-4-oxo-3-[2'-(tetrazol-5-yl)-biphenyl-4-yl-methyl]-3H-imidazo[4,5-c]pyridine or a potassium salt thereof.

6. A pharmaceutical composition comprising at least one compound of formula I according to claim 1 or a physiologically acceptable acid addition salt and a pharmaceutically acceptable carrier.

7. A method for treating angiotensin II dependent hypertension, aldosteronism or cardiac insufficiency in mammals comprising administering to a mammal an effective amount of a compound of claim 1.

8. An imidazopyridine derivative of formula I:

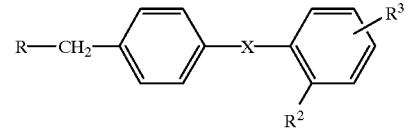

wherein

R is

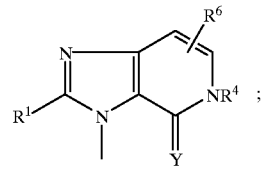

R$^1$ is A, alkenyl or alkynyl each having up to 6 C atoms;

R$^2$ is COOH, COOA, CN, NO$_2$, NH$_2$, NHCOR$^5$, NHSO$_2$R$^5$ or tetrazol-5-yl, R$^3$ is H, R$^4$ is aralkyl having 7–11 C atoms which is unsubstituted or mono- or disubstituted by Hal, $R^5$, COOH, COOA, CN, $NO_2$, $NH_2$, NHA, $N(A)_2$, $NHCOR^5$, NHCOOA, $NHSO_2R^5$, OH, OA or tetrazol-5-yl, or

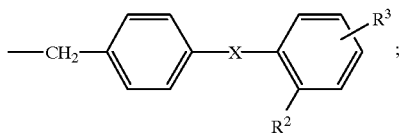

$R^5$ is alkyl having 1–4 C atoms, in which one or more H atoms can also be replaced with F;
$R^6$ is H;
X is a bond,
Y is O;
A is alkyl having 1–6 C atoms; and
Hal is Br or I, or a physiologically acceptable salt thereof.

9. A compound according to claim 8, wherein
$R^1$ is A;
$R^2$ is COOH, COOA, CN or tetrazol-5-yl; and
$R^4$ is phenyl-alkyl having 7–11 C atoms which is unsubstituted or mono- or disubstituted in the phenyl ring by Hal, $R^5$, COOH, COOA, CN, $NO_2$, $NH_2$ and/or tetrazol-5-yl, or a physiologically acceptable salt thereof.

10. A compound according to claim 9, wherein $R^2$ is tetrazol-5-yl.

11. A compound according to claim 9 wherein $R^4$ is a benzyl group which is unsubstituted or substituted by one or two of Br, COOH, COOA, CN, $NO_2$, $NH_2$ and tetrazol-5-yl.

12. A pharmaceutical composition comprising at least one compound of formula I according to claim 8 or a physiologically acceptable acid addition salt and a pharmaceutically acceptable carrier.

13. A method for treating angiotensin II dependent hypertension, aldosteronism or cardiac insufficiency in mammals comprising administering to a mammal an effective amount of a compound of claim 8.

* * * * *